US006782767B2

United States Patent
Amory et al.

(10) Patent No.: US 6,782,767 B2
(45) Date of Patent: Aug. 31, 2004

(54) GAS SAMPLE PROBE FOR A GAS ANALYZER

(75) Inventors: David Charles Amory, Branton (GB); Richard Andrew Hovan, Doylestown, PA (US); Theodore R. Barben, II, Carson City, NV (US)

(73) Assignee: Land Instruments International Limited (GB)

( * ) Notice: Subject to any disclaimer, the term of this patent is extended or adjusted under 35 U.S.C. 154(b) by 85 days.

(21) Appl. No.: 10/078,186

(22) Filed: Feb. 19, 2002

(65) Prior Publication Data
US 2002/0121147 A1 Sep. 5, 2002

(30) Foreign Application Priority Data
Mar. 2, 2001 (GB) .............................. 0105126

(51) Int. Cl.[7] .............................. G01N 1/22; G01N 1/42
(52) U.S. Cl. .................... 73/863.12; 73/31.07
(58) Field of Search .................... 73/863.11–863.22, 73/23.2, 31.07

(56) References Cited

U.S. PATENT DOCUMENTS

| | | | | |
|---|---|---|---|---|
| 3,358,653 A | * | 12/1967 | Goitein ................ | 128/204.25 |
| 3,449,567 A | * | 6/1969 | Brown ................ | 250/288 |
| 4,078,289 A | * | 3/1978 | Richter, Jr. ............ | 29/890.16 |
| 4,337,669 A | | 7/1982 | Chatzipetros et al. .... | 73/863.11 |
| 5,501,080 A | | 3/1996 | McManus et al. ...... | 73/83.11 X |

FOREIGN PATENT DOCUMENTS

| | | | | |
|---|---|---|---|---|
| DE | 9302840 | | 4/1993 | .......... G01N/1/28 |
| DE | 19527557 A1 | * | 2/1996 | .......... G01N/1/22 |
| GB | 2329459 | | 3/1999 | .......... F25D/5/02 |

* cited by examiner

Primary Examiner—Thomas P. Noland
(74) Attorney, Agent, or Firm—Trexler, Bushnell, Giangiorgi, Blackstone & Marr, Ltd.

(57) ABSTRACT

A gas sampler (1) for a portable gas analyser, having a cooler or chiller (8) through which cooler or chiller (8) the gas sample is passed prior to being conveyed to a gas analyser, has the cooler or chiller (8) operable by means other than electrical power. The invention also includes a portable gas analyser provided with such a sampler (1).

10 Claims, 5 Drawing Sheets

GAS SAMPLE PROBE FOR A GAS ANALYZER

Related/Priority Application

This application claims priority with respect to British Application No. 0105126.7, filed Mar. 2,2001.

FIELD OF THE INVENTION

This invention relates in a first aspect to a gas sampler for a portable gas analyser, and in a second aspect to an analyser provided with such a sampler.

BACKGROUND OF THE INVENTION

Portable gas analysers are known for use in the measurement of the concentration of gas in stacks and ducts of industrial processes for the purpose of emissions monitoring, and combustion control. In practice, the analyser extracts a small amount of gas from the flue usually via metal tube or probe mounted in the stack or duct and a length of hose. In order to assure accuracy of measurement, it is necessary to remove the water content from the gas, usually by means of a cooler. Traditionally such coolers require electrical power (usually mains), are bulky and not very practical to use with a portable analysers which are usually battery powered.

OBJECT OF THE INVENTION

A basic object of the invention is the provision of an improved gas sampler and portable gas analyser.

SUMMARY OF A FIRST ASPECT OF THE INVENTION

According to a first aspect of the invention, there is provided a gas sampler for a portable gas analyser, wherein the sampler comprises an integral cooler or chiller operable by means other than electrical power, through which cooler or chiller the gas sample is passed prior to being conveyed to a gas analyser.

SUMMARY OF A SECOND ASPECT OF THE INVENTION

According to a second aspect of the invention, there is provided a battery powered, portable gas analyser in combination with a sampler in accordance with the first aspect.

ADVANTAGE(S) OF THE INVENTION

The integration of a non-electrically powered cooler or chiller into the sampler firstly ensures that the required removal of water vapour from the gas sample may be satisfactorily achieved before the sample is introduced into the analyser, thereby avoiding inaccurate analysis due to the presence of water vapour, and secondly ensures that there is neither a drain on the battery capacity nor a requirement for increased battery capacity for activation of the cooler or chiller, whilst the rate and volume of gas flow through the cooler or chiller can be readily adjusted on site, by known control techniques, to ensure that for whatever gas temperature is involved—which will of course vary from site to site—there is sufficient dwell time of the gas sample within the cooler or chiller, for the dew point to be attained to condense the water vapour, so that the gas sample is then left "dry", allowing the analyser to make a true "dry" measurement.

PREFERRED OR OPTIONAL FEATURES OF THE INVENTION

The sampler is provided with an industry-standard probe.

The sampler is provided with a connection eg for a flexible hose, for gas sample transfer to a gas analyser.

The cooler comprises a vessel adopted to contain a cooling agent to remove heat from the gas sample.

The cooler comprises a cooling agent reservoir.

The cooling agent is a measure of crystals to which water is then added to initiate an endothermic chemical reaction.

The crystals are of ammonium nitrate, or potassium bromide.

The crystals and water are supplied as a package, with the water in a rupturable bag.

The vessel also houses an expansion chamber for the gas sample, the chamber having an inlet, and an outlet for the gas sample, and the chamber being subjected to the cooling effect of the endothermic reaction, whereby sufficient heat is removed from the gas sample flowing through the chamber to attain the dew point.

A catch pot is associated with the expansion chamber to collect water that is condensed out of the gas sample by lowering of the temperature of the gas sample through its dew point.

The sampler is interchangeable to provide a variety of lengths.

The sampler contains an integral flue gas temperature thermocouple and a replaceable particulate filter.

The chiller contains an impinger, a water catch pot and a cooling medium reservoir.

BRIEF DESCRIPTION OF THE DRAWINGS

One example of gas sampler in accordance with the first aspect is shown in the accompanying drawings in which.

DETAILED DESCRIPTION OF THE DRAWINGS

Figure 1:
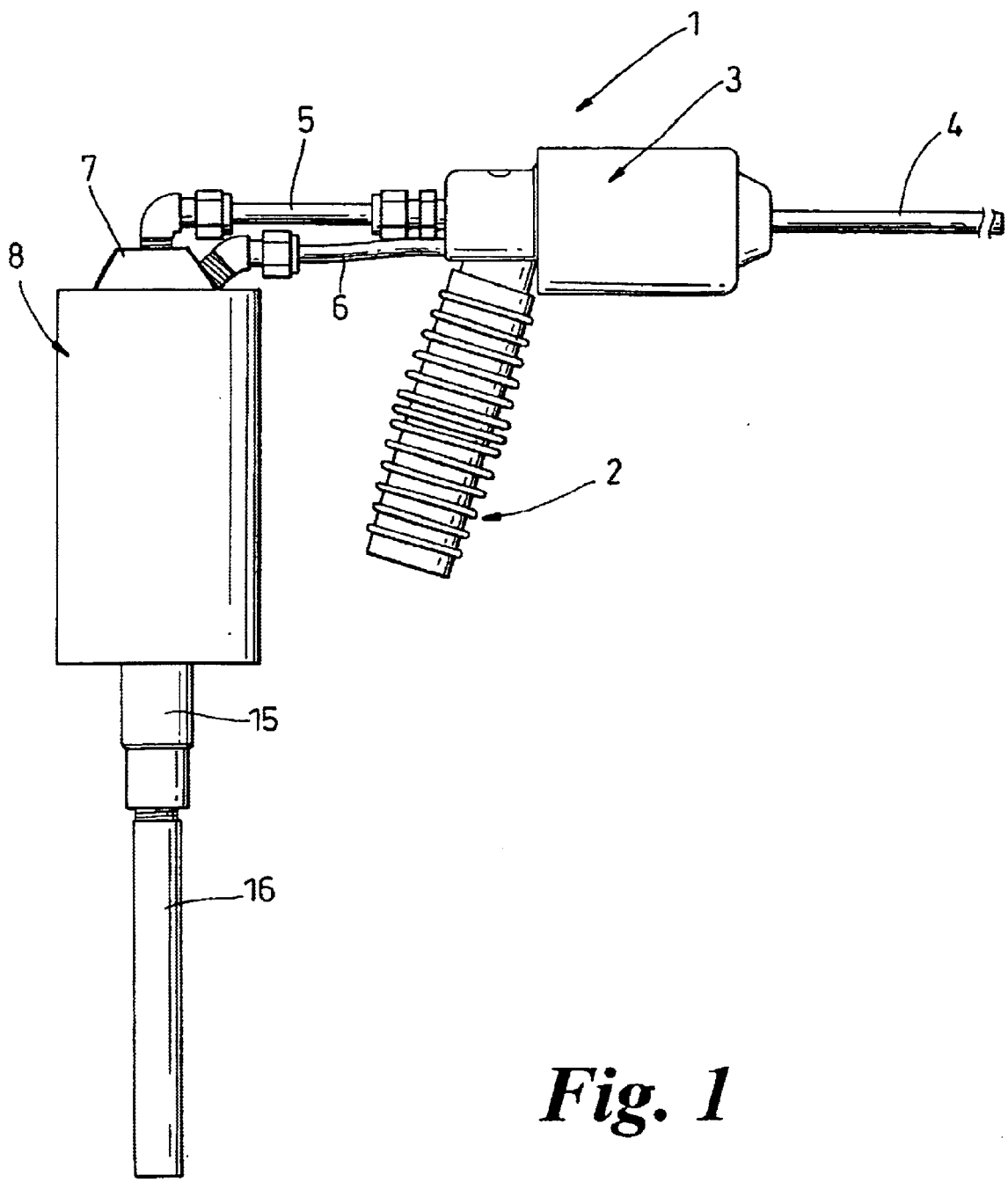
FIG. 1 is a side elevation of a gas sampler in accordance with the first aspect of the invention.
Figure 2:
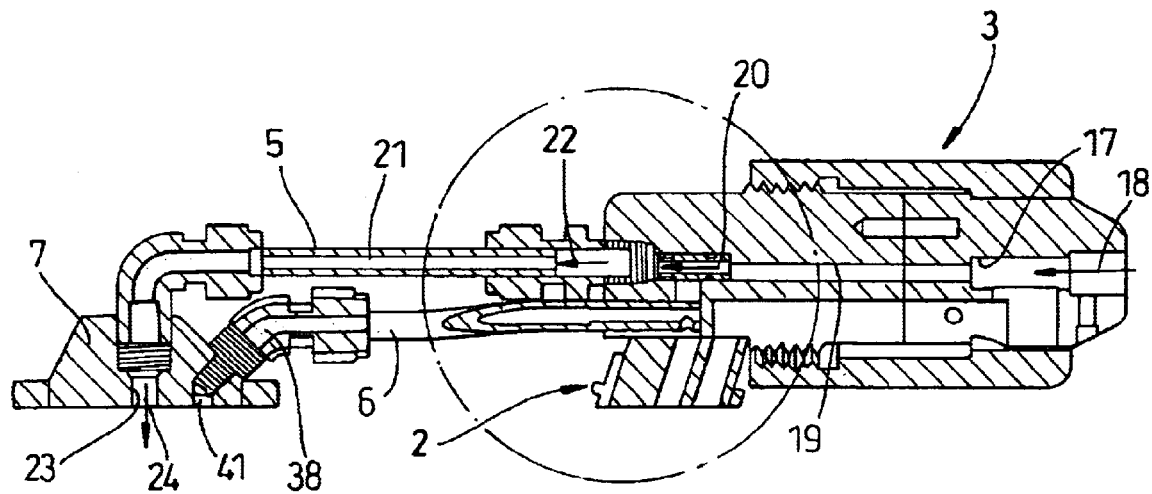
FIG. 2 is an enlarged axial, sectional view of a portion of FIG. 1, to a larger scale.

In the drawings, a gas sampler 1 comprises a handgrip handle 2 secured to a body member 3 from one end of which projects an interchangeable probe 4 adapted to collect a gas sample and to introduce the sample into the sampler 1, the latter housing an integral flue gas temperature thermocouple (not shown) and a replaceable filter (not shown) for particulates.

Figure 3:
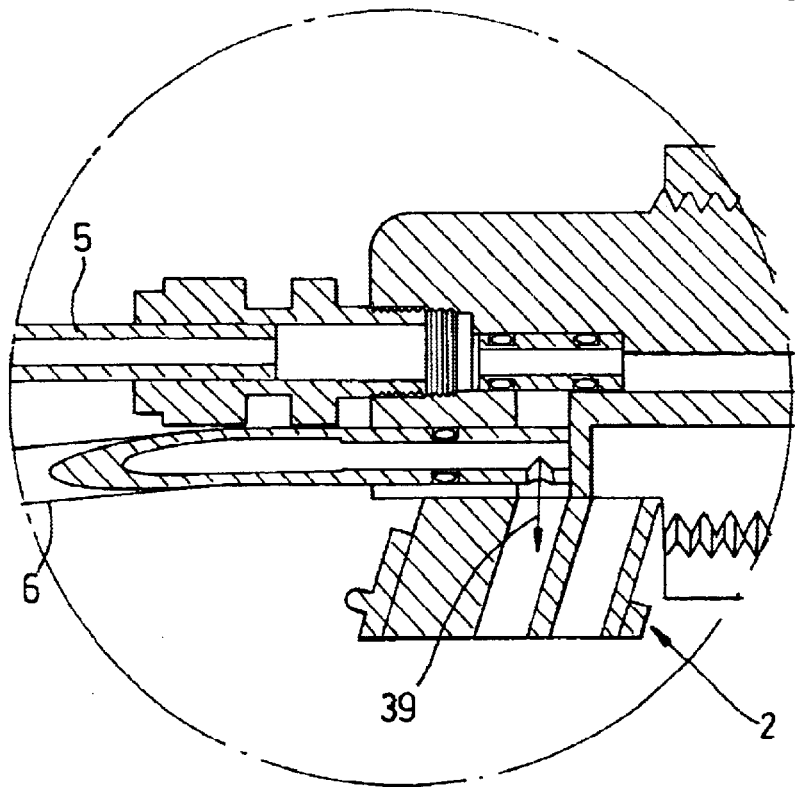
FIG. 3 is an enlarged view of a portion of FIG. 2.
Figure 4:
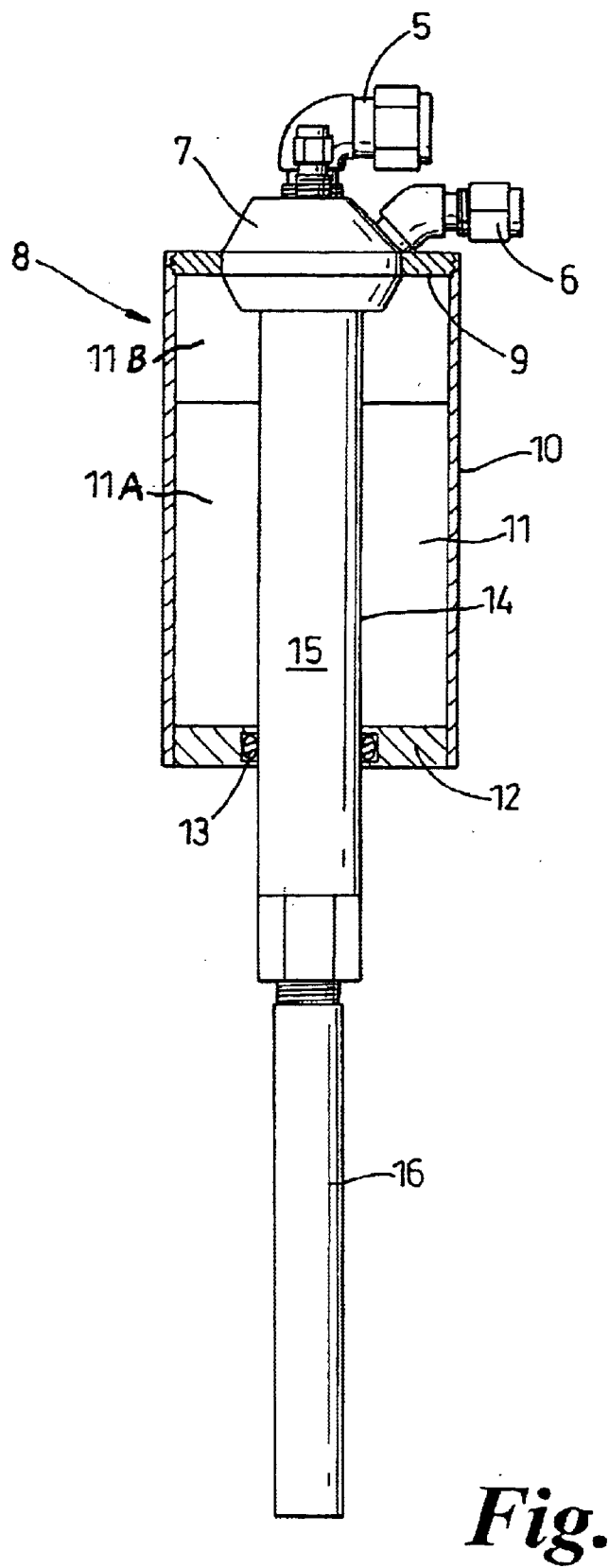
FIG. 4 is part sectional, axial view of another portion of FIG. 1.

From the other end of the body member 3 extend a hot gas inlet pipe 5, and a cold gas return pipe 6, both being attached, to a common connector 7 of a cooler or chiller 8 detailed in FIG. 3.

Figure 5:
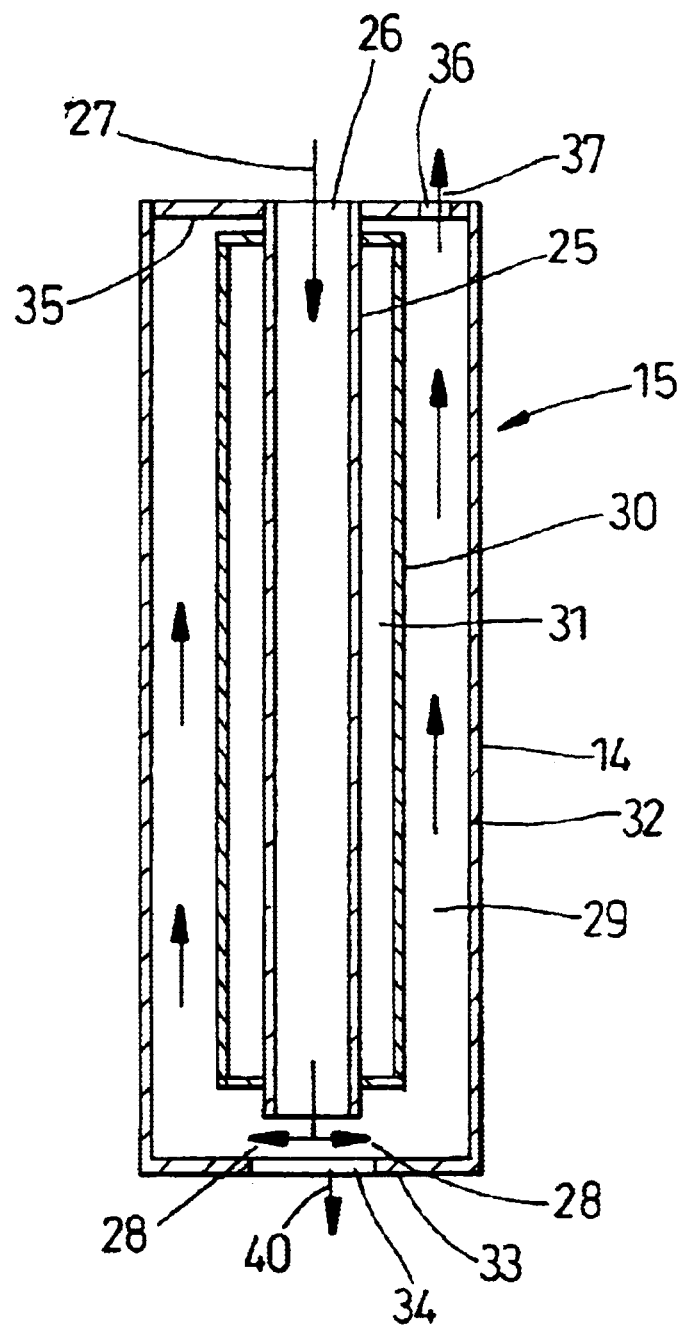
FIG. 5 is an axial sectional view, to a larger scale, through the impinger of the chiller/cooler.
Figure 6:
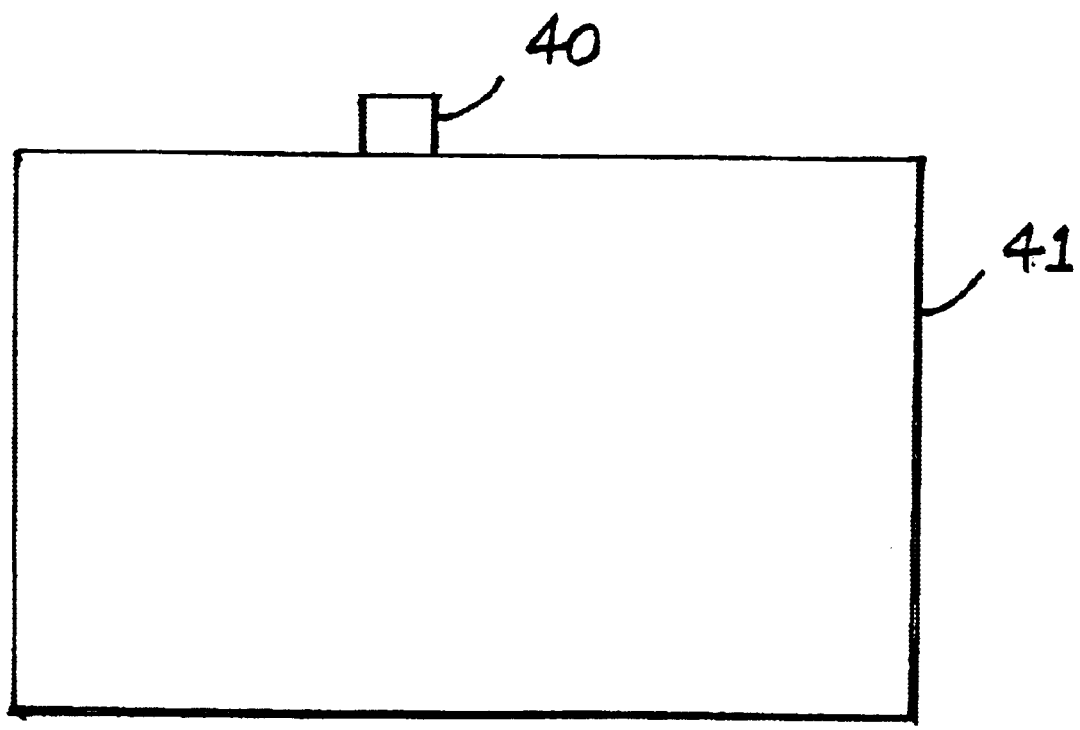
FIG. 6 is a side elevation of an industry standard portable gas analyser.

The cooler or chiller 8 comprises a top cap 9 with an external thread to which top cap is removably screwed a vessel 10 adapted to contain a cooling medium 11, the vessel 10 having a base plate 12 with an 'O'-ring 13 to seal around external periphery 14 of a co-axial impinger 15 detailed in FIG. 5, whereby the external periphery 14 is chilled by the cooling medium 11. To the lower end of the impinger 15 is attached a water catch pot 16.

In detail, a hot gas sample collected via the probe 4 enters a bore 17 of the body member 3 as indicated by arrow 18. The hot gas sample is then led to a bore 19 as shown by arrow 20. The hot gas sample then enters bore 21 of the inlet pipe 5 as shown by arrow 22, and via a bore 23 in connector 7 enters the cooler or chiller 8, as indicated by arrow 24, the cooling medium reservoir or vessel 10 having previously been filled by the operator with a cooling medium 11 eg crystals 11A and a rupturable water sachet 11B.

The hot gas sample enters tube 25 of the impinger 15 at inlet aperture 26 as indicated by arrow 27, the gas sample flowing down the tube 25 and exiting at the other end of the tube 25 as shown by arrows 28, be turned through 180° to enter an annulus 29, defined between a co-axial tube 30 attached to the tube 25 and closed off at both ends to create an annular air insulation gap 31, and co-axial outer casing 32 of the impinger 15. The casing 32 has a lower end cap 33 with an aperture 34 for drainage of water condensed out of the gas sample to the water catch pot 16 as indicated by arrow 40 and an upper end cap 35 with a cooled gas sample outlet aperture 36 for gas to exit the impinger 15 as indicated by arrow 37 and to enter the return pipe 6 via a bore 41 in the connector 7, as indicated by arrow 38.

The cold gas sample then enters the handle 2 as indicated by arrow 39.

From the handle 2, the cooled gas sample is led to a sample line (not shown) to an inlet 40 of an industry-standard gas analyser 41, with a gas outlet 42.

What is claimed is:

1. A gas sampler for a portable gas analyser, comprising an integral cooler through which a gas sample is adapted to pass prior to being conveyed to a gas analyser, wherein said cooler is operable by means other than electrical power, wherein said cooler comprises a vessel adapted to contain a cooling agent to remove heat from said gas sample, wherein said cooling agent is a measure of crystals to which water is then added to initiate an endothermic chemical reaction.

2. A sampler as claimed in claim 1, is provided with an industry-standard sample probe.

3. A sampler as claimed in claim 2, wherein said probe is interchangeable, to provide for a variety of probe lengths.

4. A sampler as claimed in claim 1, is provided with a connection for a hose for transfer of said gas sample for said sampler to a gas analyser.

5. A sampler as claimed in claim 1, wherein said crystals are of ammonium nitrate.

6. A sampler as claimed in claim 1, wherein said crystals are of potassium bromide.

7. A sampler as claimed in claim 1, wherein said crystals and water are supplied as a package, with said water in a user-rupturable bag.

8. A sampler as claimed in claim 1, wherein said vessel also houses an impinger, having an inlet aperture, and an outlet aperture for said gas sample, and said impinger is subjected to the cooling effect of said cooler, whereby sufficient heat is removed from said gas sample flowing through said cooler to attain the dew point of said gas sample.

9. A sampler as claimed in claim 8, wherein a catch pot is associated with said impinger to collect water that is condensed out of said gas sample.

10. A portable gas analyser provided with a gas sampler as defined in claim 1.

\* \* \* \* \*